United States Patent [19]

Marx

[11] Patent Number: 4,602,620
[45] Date of Patent: Jul. 29, 1986

[54] DYNAMIC OUTRIGGER EXTENSION FOR DORSAL WRIST SPLINTS

[76] Inventor: Ralph H. Marx, 7702 N. 17th Pl., Phoenix, Ariz. 85020

[21] Appl. No.: 776,404

[22] Filed: Sep. 16, 1985

[51] Int. Cl.$^4$ .............................................. A61F 5/10
[52] U.S. Cl. .................................... 128/77; 128/84 C
[58] Field of Search ................ 128/84 C, 87 A, 92 A, 128/77

[56] References Cited

U.S. PATENT DOCUMENTS

| 2,237,251 | 4/1941 | Longfellow | 128/84 C |
|---|---|---|---|
| 3,583,397 | 6/1971 | Baddour | 128/84 C |
| 3,714,940 | 2/1973 | Palmer | 128/77 |
| 3,815,587 | 6/1974 | Guerrant | 128/77 |
| 3,850,166 | 11/1974 | Tawny et al. | 128/84 C |
| 4,167,044 | 9/1979 | Girard | 128/77 |
| 4,409,970 | 10/1983 | Carrel | 128/92 A |

FOREIGN PATENT DOCUMENTS

| 45470 | 7/1910 | Austria | 128/77 |
|---|---|---|---|
| 2415227 | 10/1974 | Fed. Rep. of Germany | 128/84 C |
| 605706 | 6/1926 | France | 128/84 C |
| 879731 | 3/1943 | France | 128/84 C |

OTHER PUBLICATIONS

De Puy, "Granberry's Metacarpal & Phalanges Splint", p. 18 of 1943 catalog.

Primary Examiner—Robert Peshock
Assistant Examiner—C. W. Shedd
Attorney, Agent, or Firm—Warren F. B. Lindsley

[57] ABSTRACT

An outrigger extension for dorsal wrist splints employing adjustably positioned wheels mounted on a wire frame arranged immediately over the digits of a postoperative hand for precise alignment of dynamic splint forces following implant resection arthroplasty of the metacarpophalangeal joints.

7 Claims, 12 Drawing Figures

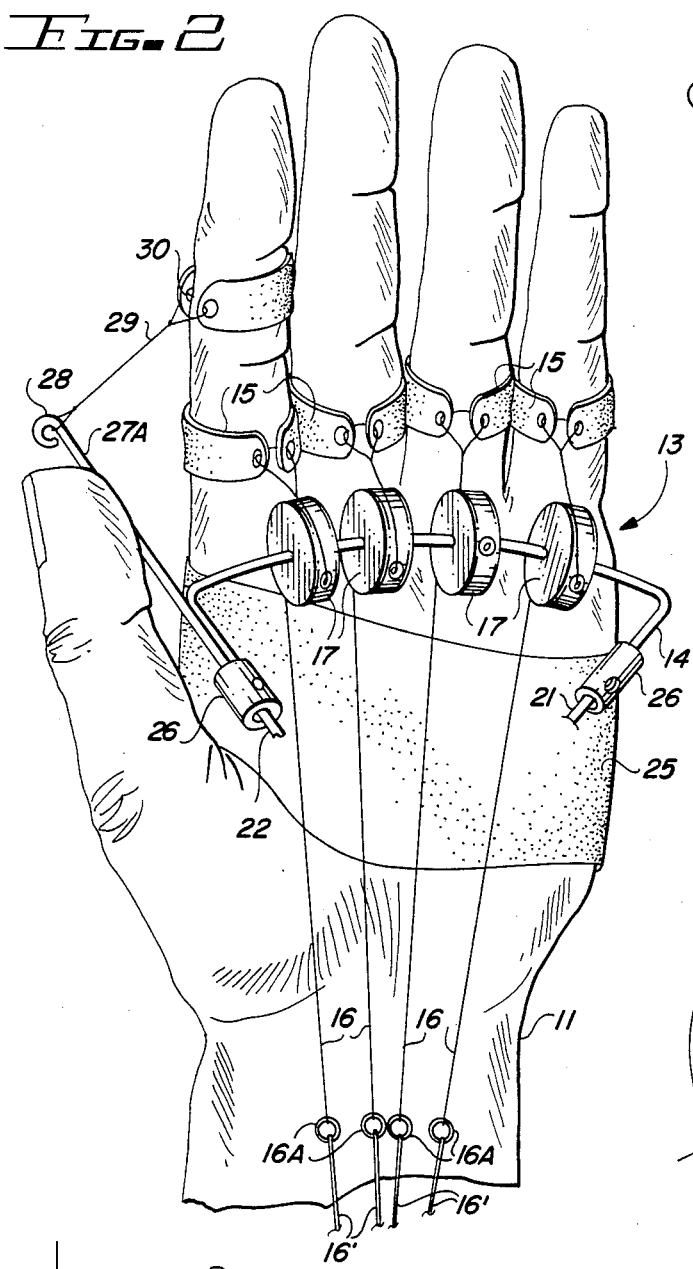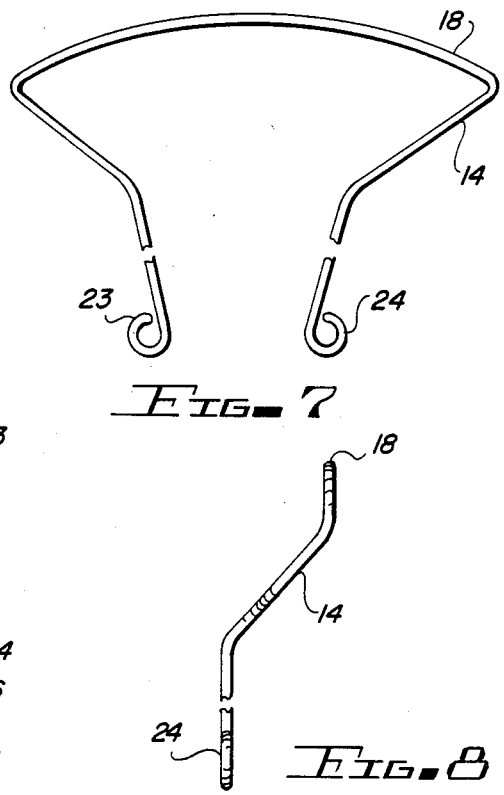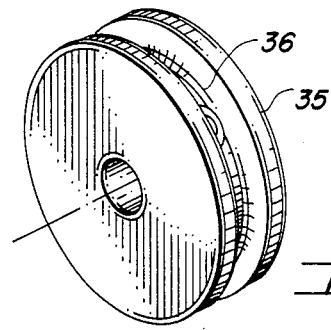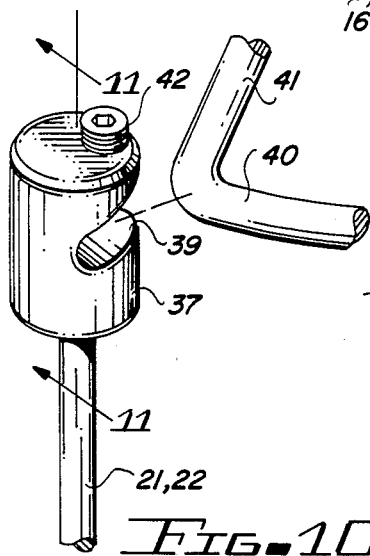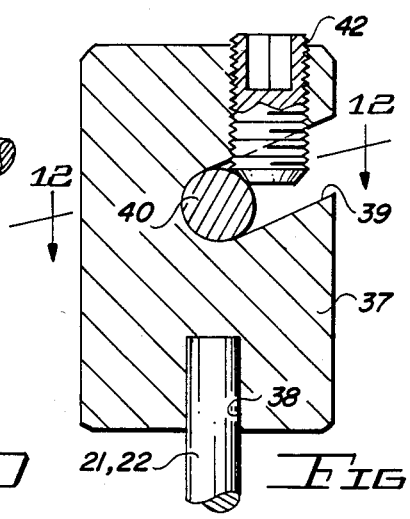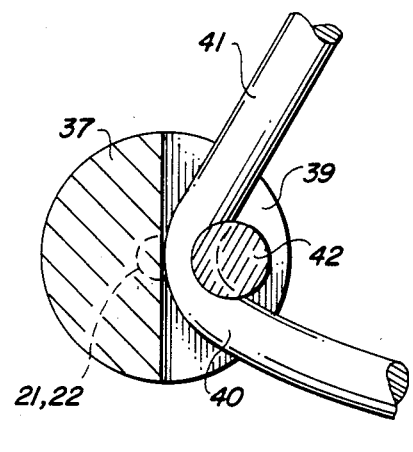

DYNAMIC OUTRIGGER EXTENSION FOR DORSAL WRIST SPLINTS

BACKGROUND OF THE INVENTION

Flexible implant resection arthroplasty of metacarpophalangeal joint in a rheumatoid hand is now a common medical procedure.

The postoperative care for the proximal interphalangeal joint depends on several factors, namely whether there was reconstruction of a stiff proximal interphalangeal joint, reconstruction of a swan-neck deformity, or reconstruction of a boutonniere deformity.

With regard to postoperative rehabilitation programs in flexible implant arthroplasty of the digits of a hand, finger slings of a dynamic brace have been used. These slings are placed on the proximal phalanges to assist metacarpophalangeal joint extension and guide alignment of the digits. The slings are adjusted to pull from radial sides to prevent ulnar deviation. Rubber bands are used with the slings to allow 70 degrees of flexion at the metacarpophalangeal joint, especially of the little finger.

If there is a tendency toward medial rotation (pronation) in the index or middle fingers, additional outrigger bars are applied to the brace to provide a rotation force at the metacarpophalangeal joints, according to the concept of a force couple, i.e., a force defined as two equal and opposite forces that act along parallel lines. This is obtained by applying a further loop to the digit that shows a tendency for pronation, and the combined pull of two slings on the one finger forms a coupling that produces a torque force in the direction of supination on the digit without interfering with flexion and extension movements.

DESCRIPTION OF THE PRIOR ART

This application is an improvement of the prior art and comprises a prefabricated dynamic extension or outrigger which is used with custom fit, thermoplastic dorsal wrist splints meeting the need for precise alignment of dynamic splint forces following implant resection arthroplasties of the metacarpophalangeal joints.

None of the known prior art involve a low profile outrigger means with finger metacarpophalangeal joint extension assists that can be easily and repeatedly adjusted after installation to accommodate changes in the hand during recovery.

SUMMARY OF THE INVENTION

Although the prior art is directed to wrist braces with finger metacarpophalangeal joint extension assists and thumb extension assist or support, none of them are directed to a low profile means employing adjustment means which may be simply and easily accomplished as often as needed without the need for skilled technicians.

It is, therefore, one object of this invention to provide a new and improved outrigger for a dorsal wrist splint.

Another object of this invention is to provide a new and improved outrigger for a dorsal wrist splint that employs means for adjustably varying the finger flexion positioning loops in a new and novel precise manner.

A further object of this invention is to provide a new and novel outrigger for providing extension assists at the proximal interphalangeal joints in a number of hand conditions that require dynamic splinting by the use of a wire form having a low profile supporting frame employing a plurality of wheels that support and adjustably position the accessories of each digit of the hand splint.

A still further object of this invention is to provide a new and improved outrigger for use with a static splint which provides low profile contact of the direction of application of dynamic tension to the fingers of a post operative hand with a plurality of wheels on the outrigger providing adjustment of the line of pull in three planes of motion.

Although one embodiment of the invention has been illustrated and described, it will be apparent to those skilled in the art that various changes and modifications may be made therein without departing from the spirit of the invention or from the scope of the appended claims.

BRIEF DESCRIPTION OF THE DRAWINGS

The present invention may be more readily described with reference to the accompanying drawings in which:

FIG. 2 is an illustration similar to FIG. 1 showing the dorsal wrist splint and associated outrigger applied to the right hand;

FIG. 7 is a plan view of the frame of the outrigger shown in FIGS. 1 and 2;

FIG. 8 is an end view of FIG.;

FIG. 9 is a perspective view of a modification of the rollers shown in FIGS. 1 and 2;

FIG. 10 is a perspective exploded view of a modification of the means for attaching the outrigger bar for preventing medial rotation of the digits to the frame of the outrigger;

FIG. 11 is a cross-sectional view of FIG. 10 taken along the line 11—11; and

FIG. 12 is a cross-sectional view of FIG. 11 taken along the line 12—12.

DESCRIPTION OF THE PREFERRED EMBODIMENT

Figure 1:
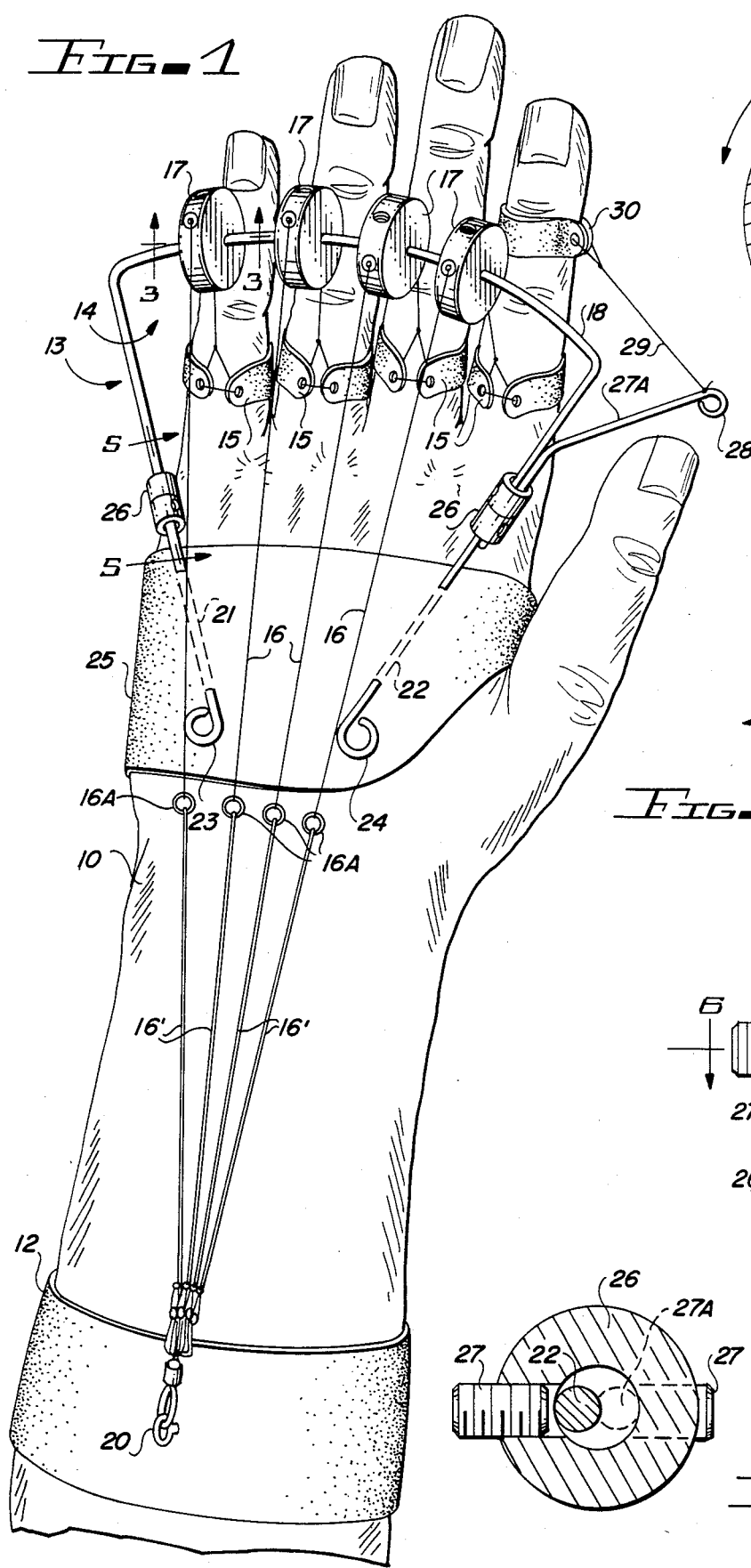
FIG. 1 is a perspective view of a left hand illustrating the use of a dorsal wrist splint and showing the use therewith of a dynamic outrigger embodying the invention.
Figure 3:
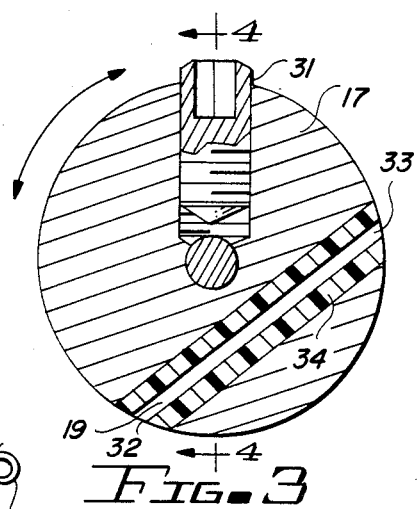
FIG. 3 is a cross-sectional view of FIG. 1 taken along the line 3—3.
Figure 4:
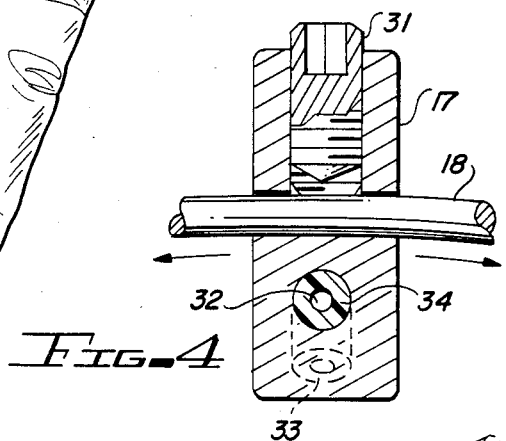
FIG. 4 is a cross-sectional view of FIG. 3 taken along the line 4—4.
Figure 5:
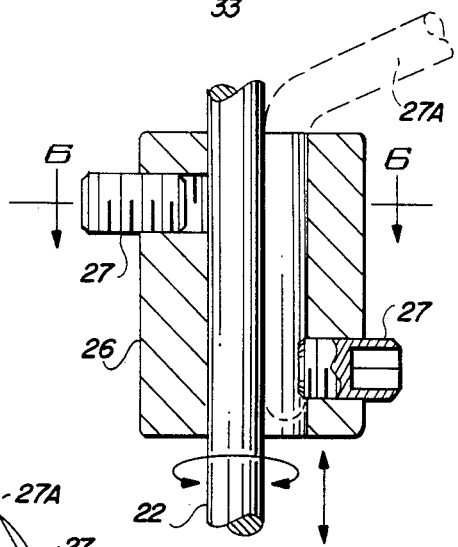
FIG. 5 is a cross-sectional view of FIG. 1 taken along the line 5—5.
Figure 6:
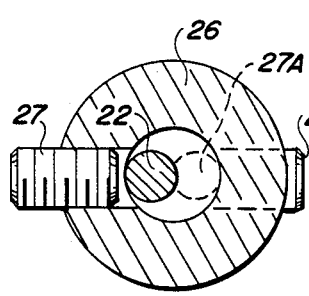
FIG. 6 is a cross-sectional view of FIG. 5 taken along the line 6—6.

Referring more particularly to the drawings by characters of reference, FIGS. 1 and 2 disclose the left and right hands 10 and 11 which might be post operative after a flexible implant resection arthroplasty of metacarpophalangeal joint in a rheumatoid hand employing dorsal wrist splints 12 having mounted thereon a dynamic outrigger extension 13 hereinafter called an outrigger. This outrigger is particularly useful with custom fit, low temperature thermoplastic dorsal wrist splints and is designed to meet the need for precise alignment of dynamic splint forces following implant resection arthroplasties of metacarpophalangeal joints. This outrigger is also useful in providing extension assist at the proximal interphalangeal joints in hand conditions requiring dynamic splinting.

The outrigger comprises a low profile supporting frame 14 formed of, for example, 0.075 inch stainless steel wire which is preformed so that when used, forms a low profile support frame approximately one inch in height above the hand, approximately three inches proximal to distal and approximately four inches in width. The transverse portion may be shaped in an arc to accommodate the differences in relative lengths of the metacarpals. This feature makes it possible for outrigger 13 to be fitted to the dorsal wrist splints used in either hand.

In order to control the pressure on each finger or digit of the hand, a plurality of slings or finger cuffs 15 are provided, one for each digit. These cuffs may be formed of 1 inch by 3 inch strips of suede material which are grommeted at each end of the 3 inch strip for receiving one end of a line 16 such as, for example, a 20 lb. test nylon leader fish line which is tied at the cuffs, as shown, and each fed off center through a roller of wheel 17 which is adjustably attached to the cross arm 18 of frame 14. Line 16 continues through the off center lined passageway 19 of wheel 17, a part of which may comprise a dynamic member such as a rubber band 16', to wristband 12 and a ring 20 secured thereto. At this point, each line associated with a given digit is suitably anchored to band 12.

As noted from FIGS. 1 and 2 of the drawings, frame 14 formed in a U-shaped configuration is further provided with a pair of legs 21 and 22 to which the ends of cross arms 18 are attached. The free ends 23, 24 of the legs 21, 22 are suitably secured to a wraparound collar 25 covering a part of the palm and back of the hand. The ends may be held thereto by any suitable means such as cement, rivets, glue or any suitable overwrapping of the collar.

The free ends 23 and 24 are spaced apart the distance of the width of a hand and extended in the same direction in a common plane. At a common point along their lengths, they are distorted to position their other ends in a second plane parallel with the first plane.

A coupler 26 is provided for the outrigger which is attached to either leg 21 or 22 of frame 14 by a suitable set screw 27, as shown in FIGS. 1 and 2. This coupler is intended to secure a rod 27A thereto in parallel arrangement with the associated leg of frame 14 which rod has an eyelet 28 at its free end. A line 29 is attached at one end to eyelet 28 and at its other end to a further cuff 30 wrapped around the extremity of one of the digits of hand 10 or 11. The force or tension applied to cuff 30 is intended to prevent medial rotation in the index or middle fingers as heretofore explained.

Each wheel 17 may be formed of aluminum weighing about ⅛ of an ounce employing an 8/32 of an inch stainless steel set screw 31 for detachably securing the wheel to cross arm 18 of frame 14. The off center passageway 19 extends through the wheel to provide surface or rim openings 32 and 33 at approximately a 90 degree angle to each other. The shaft, as shown, may be lined with 0.095 inch plastic tubing 34 to reduce friction and to eliminate sharp edges at the openings 32 and 33.

USE OF OUTRIGGER

The outrigger is attached to a custom fit dorsal wrist splint. The technique of splint fabrication will not be discussed except to point out that a dynamic splint must have a properly fit static portion. Use of the prefabricated outrigger with a custom splint provides means to simplify construction, to give maximum adjustability of dynamic forces, and at the same time, to achieve optimum comfort and stability.

The outrigger is placed over the dorsum of the hand so that the most distal point of the arc rests over the mid portion of the proximal phalanx and the slope of the arc aligns with the mid portion of the adjacent proximal phalanges.

In some instances, particularly very small hands, the proximal wire must be bent to conform to the shape of the splint over the dorsum of the hand. If a bulky dressing is used over the dorsum of the hand, the wire frame may be bent so that a low profile is maintained.

A helpful technique for attaching the outrigger is to heat the proximal wire with a heat gun, then place it while the splint is on the hand. This accurately marks the point of attachment. Generally, the wire will adhere to the splint while an overlapping piece of thermoplastic material is bonded and/or riveted to secure the outrigger.

A 5/64 inch hex wrench is used to release the set screws in the wheels. The wheels are designed to slide radially and ulnarly. They also spin to provide ¾" of proximal and distal adjustment. Some specialists recommend for implant resection arthroplasties of the MF joints that slings of the postoperative splint be adjusted to pull from the radial side. Others advocate that the pull be in direct alignment and that the digits are neither radially nor ulnarly devisted.

The spin of the wheel allows adjustment of the angle of pull at 90 degrees to the proximal phalanx, the optimal angle to minimize traction and compression forces.

If rotation of a digit is needed, the radial outrigger is used. The combined pull of two slings creates a force couple to supinate the finger.

The metal or thermoplastic hook 20 attached to splint 12 over the proximal forearm provides the point of attachment for rubber bands or the nylon fish line 16. One advantage of low profile splinting is that it provides as long a length over which to stretch line 16 as possible, therefore providing more constant tension. This constant tension is particularly helpful following implant resection arthroplasties since the resistance to extreme flexion remains low.

The disclosed outrigger is useful in dynamic extension splinting of the digits, particularly following implant resection arthroplasties. The splint's low profile design reduces the resistance to flexion and friction is negligible at the transverse bar. It provides superior adjustability of the angle of pull both laterally and proximal-distal. This allows precise initial alignment of the dynamic extension forces as well as simplified ongoing adjustment to accommodate changes in the hand.

Because it is adaptable for right or left and small to large hands, the expense of keeping a large number of splints in supply is eliminated. The outrigger is used with a custom fit splint, therefore providing some measure of the convenience and time savings of a prefabricated splint as well as the superior comfort and stability of a custom splint.

FIG. 9 discloses a modified version of wheel 17, wherein wheel 35 is provided with a groove 36 around its outer periphery for guiding line 16. As noted, the openings of passageway 19 open into the groove.

FIGS. 10–12 disclose a further means of attaching rod 27A to the legs of frame 14.

As shown, a novel coupling 37 may be suitably secured to the ends of legs 21 and 22 of frame 14 by insertion of one of their ends into opening 38 in coupling 37. The outer periphery of the coupling is notched at 39 for receiving a bend or elbow portion 40 of a rod 41 serving the function of rod 27A of FIGS. 1 and 2. Elbow 40 is held in notch 39 by a set screw 42 and may be readily removed or adjusted without disturbing the connection of coupling 37 to the legs of frame 14.

Although but a few embodiments of the invention have been illustrated and described, it will be apparent to those skilled in the art that various changes and modifications may be made therein without departing from the spirit of the invention or from the scope of the appended claims.

What is claimed is:

1. An outrigger for use with a dorsal wrist splint for precise alignment of dynamic splint forces following implant resection arthroplasty of the metacarpophalangeal joints of a hand comprising:
    a low profile supporting wire frame having two spaced apart legs extending in the same direction and positioned at one end in the same plane, said legs being distorted at a common point along their lengths to position their other ends in a second plane parallel with said first plane,
    said frame comprising a transverse portion interconnecting said other ends,
    said transverse portion comprising an arcuate configuration extending outwardly of said other ends to accommodate the differences in lengths of the metacarpals of the hand,
    a plurality of wheels axially mounted on said transverse portion, one juxtapositioned to each digit of the hand on which said outrigger is mounted,
    said wheels being adjustably positioned radially of and longitudinally along said transverse portion,
    each of said wheels being provided with means for guiding a line, attached to an associated digit, to a wristband on the hand on which the outrigger is mounted for controlling the position of the digit.

2. The outrigger set forth in claim 1 wherein:
    said transverse portion lies in the same plane as said other ends of said legs.

3. The outrigger set forth in claim 1 wherein:
    each of said wheels is provided with means for guiding a line attached to an associated digit,
    said means comprising an off-center passageway extending through said wheel in a direction spaced from and perpendicular to the axis of the wheel for holding the line on the wheel and guiding it therethrough.

4. The outrigger set forth in claim 3 wherein:
    the ends of said passageway are spaced approximately 90 degrees from each other.

5. The outrigger set forth in claim 4 in further combination with:
    a liner for covering the interior of said passageway.

6. The outrigger set forth in claim 1 wherein:
    each of said wheels is provided with a set screw extending through the peripheral edge of the wheel for engaging said transverse portion of said frame to adjustably position said wheel thereon.

7. The outrigger set forth in claim 1 in further combination with:
    a coupler mounted on one of said legs,
    a rod secured and positioned by said coupler to extend laterally outwardly from said one of said legs, and
    means attached to the free end of said rod for attaching to one of said digits to provide a force coupling to supinate said digit.

* * * * *